(12) United States Patent
Tumey et al.

(10) Patent No.: US 6,488,643 B1
(45) Date of Patent: Dec. 3, 2002

(54) WOUND HEALING FOOT WRAP

(75) Inventors: David M. Tumey, San Antonio, TX (US); L. Tab Randolph, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 09/168,598

(22) Filed: Oct. 8, 1998

(51) Int. Cl.$^7$ .................................................. A61F 13/00
(52) U.S. Cl. .............................. 602/13; 602/23; 602/30; 601/150
(58) Field of Search .............................. 602/13, 30, 23; 601/150, 152

(56) References Cited

U.S. PATENT DOCUMENTS

| | | | |
|---|---|---|---|
| 3,245,405 A | * 4/1966 | Gardner | |
| 3,920,006 A | 11/1975 | Lapidus | 128/24.1 |
| 4,614,179 A | 9/1986 | Gardner et al. | 128/64 |
| 4,738,257 A | 4/1988 | Meyer et al. | 128/156 |
| 5,031,604 A | 7/1991 | Dye | 128/64 |
| 5,115,801 A | 5/1992 | Cartmell et al. | 602/48 |
| 5,176,663 A | 1/1993 | Svedman et al. | 604/305 |
| 5,244,457 A | 9/1993 | Karami et al. | 602/55 |

OTHER PUBLICATIONS

Caputo, G.M. et al., The Total Contact Cast: A Method for Treating Neuropathic Diabetic Ulcers, American Family Physician, Feb. 1, 1997, 605–11 and editorial 425–26.
Cherry, G.W. et al., Bandaging in the Treatment of Venous Ulcers: A European View, Ostomy/Wound Management, Nov./Dec. 1996, 13S–18S.
Mayrovitz, H.N. et al., Effects of Compression Bandaging on Lower Extremity Skin Microcirculation, WOUNDS, Nov./Dec. 1996. 200–07.
Phillips, T., Leg Ulcer Management, Dermatology Nursing, Oct. 1996, vol. 5, No. 8, 333–40.
Sieggreen, M.Y. et al., Managing Leg Ulcers, Nursing, Dec. 1996, 41–46.
U.S. Patent Application No. 08/039,574 filed Mar. 25, 1993.
Kinetic Concepts, Inc., The Plexipulse All in 1 System, Date Unknown.
Rastgeldi, S. Article in Two Parts: "I. Pressure Treatment of Peripheral Vascular Disease," and "II. Intermittent Pressure Treatment of Peripheral Vascular Disease, A Survey of Sixteen years Personal Experience," published in Opuscula Medica, Supplemetum XXXVII 1972, Gundad av Sixten Kallner 1956.

* cited by examiner

*Primary Examiner*—John G. Weiss
*Assistant Examiner*—Kelvin Hart

(57) ABSTRACT

A medical wrap for the promotion of diabetic and like wound healing generally comprises a multi-layered sheet structure for removable application to a patient's foot, said sheet structure having interposed therein an integral bladder; an inlet for fluid inflation of said bladder; and said sheet structure being adapted and said bladder being shaped to produce a non-shearing compressive force in the area of the patient's first and fifth metatarsal heads upon fluid inflation of said bladder. The multi-layered sheet structure may comprise a first sheet and a second sheet, said first sheet forming the exterior of said structure and said second sheet forming the interior of said structure, said second sheet being more extensible than said first sheet. A padding layer of ester foam, or the like, may also be incorporated into each sheet.

5 Claims, 2 Drawing Sheets

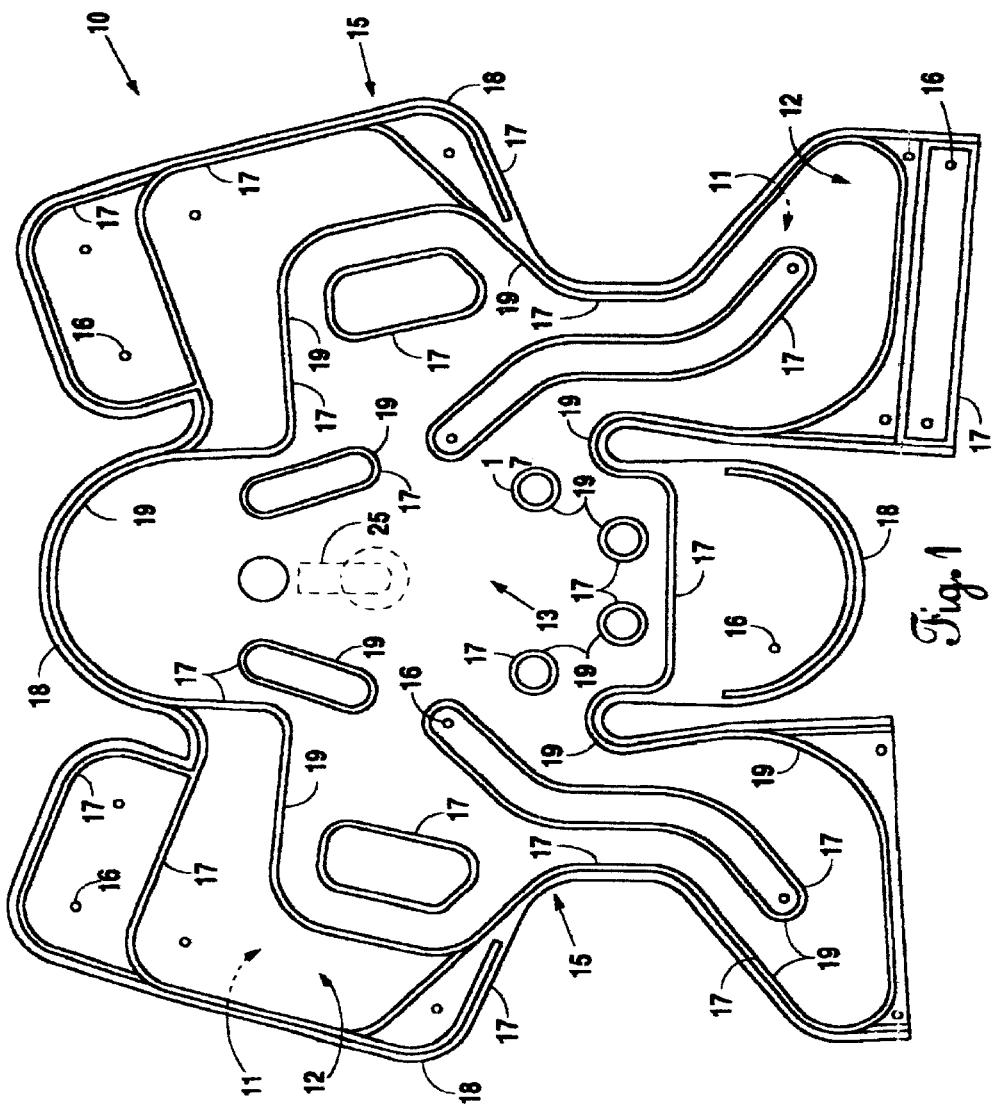

WOUND HEALING FOOT WRAP

FIELD OF THE INVENTION

The present invention relates to wound healing devices. More particularly, the invention relates to a therapeutic foot wrap for application of positive pressure to the first and fifth metatarsal head and heel regions of a patient suffering diabetic ulceration and/or like wounds.

BACKGROUND OF THE INVENTION

An ulcer is commonly defined as a lesion on the surface of the skin, or on a mucous surface, manifested through a superficial loss of tissue. Ulcers are usually accompanied by inflammation and often become chronic with the formation of fibrous scar tissue in the floor region. Chronic ulcers are difficult to heal; they almost always require medical intervention and, in many cases, lead to amputation of the limb upon which they occur.

In general, ulcers may be attributed to any of a variety of factors reducing superficial blood flow in the affected region. Leg (including the foot) ulcers, in particular, are attributable to congenital disorders, external injury, infections, metabolic disorders, inflammatory diseases, ischaemia, neoplastic disorders and, most commonly, arterial disease, neuropathic disorders and venous insufficiency. Neuropathic and ischaemic ulcers commonly manifest in association with diabetes and, for this reason, are often referred to as diabetic ulcers. Although certainly not exhaustive, the table entitled Common Etiology of Leg Ulcers, highlights the frequency at which patients are placed at risk for the formation of this potentially devastating disease.

| Common Etiology of Leg Ulcers | |
|---|---|
| Congenital: | Absence of valves, chromosomal disorders, Klinefelter's syndrome, connective tissue defects affecting collagen and elastic fibers, arteriovenous aneurysms, prolidase deficiency. |
| External Injury: | Laceration, contact dermatitis, decubitus, inoculation (drug addiction), burns, cold, irradiation. |
| Infections: | Viral, bacterial, fungal. |
| Metabolic Disorders: | Diabetes mellitus, colonic stasis from sugar/fats. |
| Inflammatory Diseases: | Vasculitus, pyoderma gangrenosum, rheumatoid arthritis, panniculitus. |
| Ischaemia: | Peripheral vascular disease, embolus, scleroderma hypertension, sickle-cell anemia. |
| Neoplastic Disorders: | Skin neoplasms, leukemia. |
| Neuropathic Disorders: | Spina bifida, leprosy, diabetes mellitus, neoropathy syringomyelia. |
| Venous Insufficiency: | Posture (prolonged standing, legs crossed, long legs), abdominal pressure (tumor, pregnancy), employment, physical activity (apathy, paralysis, osteoarthritis), effort (weight lifting), deep vein thrombosis (50% tibial fractures, 25% abdominal surgery, 25% myocardial thrombosis, 50% strokes), blood stasis, hemolytic anemias. |

Perhaps as striking as the incidence of this disease, is the magnitude of the resources dedicated to the combat of its occurrence. It is estimated that leg ulcers cost the U.S. healthcare industry in excess of $1 billion annually in addition to being responsible for over 2 million annual missed workdays. Unfortunately, the price exacted by ulcers is not merely financial. Leg ulcers are painful and odorous open wounds, noted for their recurrence. Most tragic, diabetic ulcers alone are responsible for over 50,000 amputations per year. As alarming as are these consequences, however, the basic treatment regimen has remained largely unchanged for the last 200 years. In 1797, Thomas Baynton of Bristol, England introduced the use of strips of support bandages, applied from the base of the toes to just below the knee, and wetting of the ulcer from the outside. Standard of care treatment for ulcers affecting the foot has developed little beyond prevention oriented approaches. When management of the underlying disease condition fails to prevent ulcer formation, debridement and occlusive bandaging is about the only remaining option. As discussed in more detail herein, versions of these therapies remain the mainstay treatment to this day and, clearly, any improvement is of critical importance.

As noted above, the most common causes of leg ulcers are venous insufficiency, arterial disease, neuropathy, or a combination of these problems. Venous ulcers, in particular, are associated with abnormal function of the calf pump, the natural mechanism for return to the heart of venous blood from the lower leg. This condition, generally referred to as venous insufficiency or venous hypertension, may occur due to any of a variety of reasons, including damage to the valves, congenital abnormalities, arteriovenous fistulas, neuromuscular dysfunction, or a combination of these factors. Although venous ulcers tend to be in the gaiter area, usually situated over the medial and lateral malleoli, in severe cases the entire lower leg can be affected, resembling an inverted champagne bottle.

Diabetic and arterial ulcers, in particular, are associated with degenerative disease resulting in progressively narrowed vessel lumen which, in turn, causes obstructed blood flow. These types of ulcers are frequently found at sites of localized pressure or trauma. The diabetic patient (neuropathic ulcers), who may also suffer arterial disease, will often have impaired sensation in the foot area and will therefore likely be unaware of repeated trauma. This exacerbates ulceration in the traumatized or pressure-bearing areas, commonly the first and fifth metatarsal heads and over the heel.

Clinical modalities for prevention of venous ulcers generally focus on the return of venous blood from the lower extremities to the heart. Mechanical prophylaxes are widespread in the art of prevention and are often referred to as foot pumps or wraps, leg pumps or wraps and sequential compression devices, all of which function to prevent deep vein thrombosis ("DVT"), a common precursor to venous stasis ulcers. An exemplary foot pump is commercially available from Kinetic Concepts, Inc. of San Antonio, Tex. under the trademark "PLEXIPULSE." An exemplary sequential compression device is described in U.S. Pat. No. 5,031,604 issued Jul. 16, 1991 to Dye ("Dye").

As generally described in Dye, mechanical prophylaxes for DVT prevention are directed toward the improvement of venous return. To this end, devices like that of Dye are adapted to take advantage of the naturally occurring valvular structure of the veins to squeeze the blood from a patient's limb. For instance, the trademark "PLEXIPULSE" device is adapted to intermittently compress the patient's plantar venous plexus, promoting the return of blood from the patient's foot upward and through the calf region. Likewise, and as generally described at column 2, lines 33 et seq. of Dye, leg compression devices are usually adapted to squeeze the patient's leg first near the ankle and then sequentially upward toward the knee. This milking-type sequence may or may not be performed on a decreasing pressure gradient, but is always designed to move blood from the extremity toward the heart. It should be noted at this time that these types of devices are generally not appropriate for use in the intended function of the present invention as the described wraps tend to produce a shearing force in the region of the first and fifth metatarsal heads and over the heel.

Treatment of venous ulcers, on the other hand, is predominately centered about gradient compression, through bandaging, and leg elevation. Although it is not precisely known how or why they improve venous ulcer healing, compression therapies, specifically including compression bandaging techniques, are now the well-established mainstay for the treatment of venous stasis and other ulcers. In fact, it is generally undisputed that compression bandaging is the most efficacious method for wound healing, often resulting in overall improvement of the patient's quality of life.

Among the predominant theories for explaining the effects of compression bandaging, edema reduction and control for the improvement of venous hemodynamic abnormality concomitant prolonged venous hypertension from valvular incompetency or dysfunction stands out. It is thought that the reduction and control of edema improves capillary microcirculation, in turn resulting in the elimination of venous ulcers. Another popular theory holds that reactive hyperemia is responsible for the success of compression bandaging. According to this theory, the arrest and subsequent restoration of blood flow to the affected region, known as Bier's method, results in an ultimately increased presence of blood in the region. Regardless of the theory adopted, however, it is important to note that it is universally understood that a proper gradient must be established in order to derive the benefits of compression bandaging. This gradient is generally accepted as being from about 35 to 45 mm Hg at the ankle and reducing to about 15 to 20 mm Hg at just below the knee. Often stated in the literature as a prerequisite to good bandaging technique, the maintenance of graduated compression is critical to effective treatment of ulcers. Failure to initially obtain, and thereafter maintain, the desired sub-bandage pressures is fatal to the treatment regimen.

The criticality of establishing and maintaining the desired sub-bandage pressure directly results in significant disadvantages, associated with the application of compression bandaging in general, and serious hazards to the patient, associated with the misapplication of bandaging specifically. In particular, proper bandaging under the presently known methods requires a highly skilled caregiver in order to establish the desired sub-bandage pressures. Once established, however, the pressure gradient is difficult to monitor. In fact, the sub-bandage pressure is usually only monitored to the extent that the caregiver either observes or fails to observe a reduction in edema. This is particularly disturbing when one considers that it is to be expected that as properly applied bandaging performs its intended function edema will be reduced causing, in effect, the bandage to become loosened to a state of improper application where after edema will probably increase. More disturbing is the fact that over tightening of the bandage places the patient at direct risk for skin necrosis and gangrene, especially if the patient has arterially compromised limbs.

Unfortunately, there has been surprisingly little development in treatment protocols directed toward better achieving desired sub-bandage pressures. Even though the foregoing discussion highlights the necessity for frequent reapplication of the bandaging, the presently available treatment modalities are very difficult to apply. One common type of bandaging comprises four layers, including an orthopedic wool layer, a crepe bandage layer and two compression layers. The compression layer bandages are often provided with imprinted rectangles that become square upon achieving the correct tension. Although helpful, only two sets of markings are typically provided—one for normal size ankles and one for larger, and no provision is made for adaptation to changes in the level of edema. Another common treatment modality is the compression dressing—an elastic support stocking providing a compression of about 30 to 40 mm Hg. These stockings, however, are often impractical for elderly patients or patients with arthritis who may find them difficult to put on the leg and for the patient with large or exudative ulcers, which require frequent dressing changes, compression stockings are thought to be prohibitively impractical. While the foregoing discussion makes clear that the theory of compression bandaging, albeit limited in application, is sound for the treatment of wounds, it is unfortunately very difficult to extend to treatment of wounds on or about the feet. Compression bandages simply are not readily adapted for application to a foot.

As this discussion makes apparent, the need for treatment modalities beyond the presently known compression bandaging techniques is great. Unfortunately, the mechanical prophylaxes utilized in prevention therapies are not generally extendable to wound healing. Although, recent reports have indicated that achieving sustained sub-bandage pressures near 40 mm Hg may be more efficacious in providing timely wound healing than lower pressure levels and the present applicant has found that mechanical prophylaxes are generally better able to deliver higher pressures, caution is warranted. Because some 20 percent or more of patients with venous ulcers may also have some degree of co-existing lower extremity arterial disease, it is important to clarify the possible impact of higher levels of compression bandaging on lower extremity skin circulation. Studies show that mechanically produced compression levels may produce ischaemic not noted at similar compression levels obtained through bandaging. The reductions in leg pulsatile blood flow associated with mechanical prophylaxes often occur at compression levels below that necessary for good bandaging effects. This result, sometimes called cuffing, has resulted in most mechanical prevention prophylaxes being contraindicated for patients exhibiting DVT. Consequently, those of ordinary skill in the art have to date steadfastly avoided mechanical prophylaxes for the treatment of venous stasis and other ulcers or edema of the extremities.

The end result is that the patient once suffering from diabetic ulcers is left at the mercy of an extraordinarily high recurrence rate and is thought to be at severe risk for eventual amputation. This leads to emotional complication of the treatment process. Because preventing recurrence is as great a challenge as healing the ulcer, new and improved methods and apparatus for treatment of leg ulcers are desperately needed. In addition, because careful skin care and compression therapy must continue throughout the patient's lifetime, it is imperative to the patient's long-term health care to provide a low-cost, easily applied solution with which the patient may be assured of receiving effective therapy.

Additionally, many other problems, obstacles and challenges present in existing modalities for the treatment of leg ulcers will be evident to caregivers and others of experience and ordinary skill in the art. With the severe shortcomings of the prior art in mind, it is an overriding object of the present invention to improve generally over the prior art in providing a wound treatment apparatus that is adaptable to the changing physiology of a patient, is simple to use and is sure to produce the desired treatment.

SUMMARY OF THE INVENTION

In accordance with the foregoing objects, the present invention—a foot wrap for the promotion of healing ulcers and like wounds of the foot—generally comprises a multi-layered sheet structure for removable application to a patient's foot, having interposed therein an integral bladder, and an inlet for fluid inflation of the bladder. The sheet structure is preferably adapted and the bladder is preferably shaped to produce a non-shearing compressive force in the area of the patient's first and fifth metatarsal heads upon fluid inflation of the bladder.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein:

FIG. 1 shows, in plan view, the foot wrap of the present invention, detailing its construction.

DETAILED DESCRIPTION OF PREFERRED EMBODIMENT

Figure 2A:
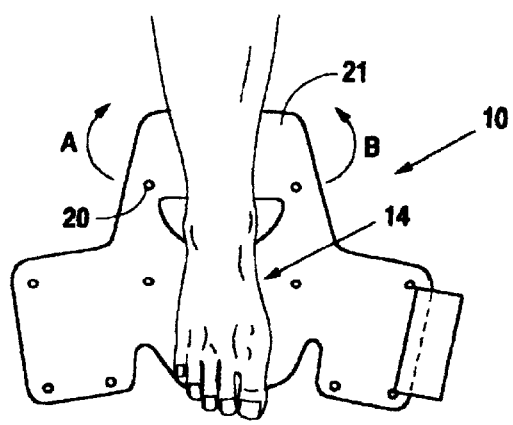
FIGS. 2A through 2C show, in perspective views, the application of the foot wrap of the present invention to a patient's foot.

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Referring to the figures, the present invention generally comprises a foot wrap 10 adapted to apply a compressive pressure to the first and fifth metatarsal head regions of a patient's foot. In particular, the wrap 10 imparts a compressive force to the region of the heel and forward to beneath the phalanges of the toes. As will be better understood further herein, this compressive force, which is preferably applied in cyclical fashion, serves to reduce edema and produce local hyperemia and the vaso-dilator endothelium-derived relaxing factor (EDRF). Each of these results is thought to contribute to the healing of diabetic ulcers and like wounds.

The foot wrap 10 of the present invention preferably comprises a first sheet 11 and a second sheet 12 of substantially similar shape, bonded together to form a bladder 13 therebetween. As will be better understood further herein, this bladder 13 is shaped through the bonding process in order to direct the compressive force to the desired region of the patient's foot 14. The first sheet 11, which forms the exterior of the wrap, should be cut from a robust, non-stretch fabric. The second sheet 12, which forms the interior of the wrap and will be placed adjacent the patient's foot 14, should be cut from a robust but semi-elastic fabric. As will be better understood further herein, this variance in elasticity between the first sheet 11 and the second sheet 12 serves to direct the compressive action of the wrap in an inward direction toward the patient's foot 14.

Because the wrap 10 will be snugly applied to a major portion of the patient's foot 14 and may remain in place for a prolonged period, it is important that the wrap be designed to facilitate removal from the patient's skin of accumulated surface moisture. While in the preferred embodiment of the present invention, this feature is accomplished by cutting both the first and second sheets 11, 12 from an air and water impermeable but water vapor permeable fabric, it is only deemed critical that at least the second sheet be cut from such a fabric. As explained in more detail further herein, cutting the sheets 11, 12 from a vapor permeable fabric serves to allow evaporation of moisture from the foot area beneath the wrap in spite of the wrap's placement about the foot 14.

Means, as detailed in Applicants co-pending U.S. patent application entitled MEDICAL PUMPING APPARATUS AND RELATED METHODS, filed on even date herewith and naming as inventors David M. Tumey and L. Tab Randolph, by this reference incorporated herein, are provided for fluid inflation of the bladder 13 integral the two sheets 11, 12—preferably by the provision of pressurized air. Those of ordinary skill in the art will recognize, therefore, that only the interior second sheet 12 need be water vapor permeable for accumulated perspiration to be carried away by the inflating fluid. It is of course better, however, for both the first and second sheets 11, 12 to be water vapor permeable in order that accumulated perspiration may also evaporate directly to the atmosphere. With these examples in mind, those of ordinary skill in the art will recognize that other methods of moisture control may be embodied; regardless of the particular implementation, however, this important aspect in the promotion and maintenance of healthy skin condition should not be overlooked.

In order to facilitate manufacture of the foot wrap 10, each of the first and second sheets 11, 12 of the wrap 10 comprise a laminate of an RF or heat weldable film with a more substantial fabric layer. In the preferred embodiment, each laminate comprises a thin (three to eight mil) polyurethane film layer (having a low melting temperature for reasons detailed further herein) and a layer of soft fabric such as that commonly available under the trademark "LYCRA." As is known to those of ordinary skill in the art, the trademark "LYCRA" fabric is approved by the U.S. Food and Drug Administration for use in many applications requiring a fabric to contact with a patient's skin. Additionally, the trademark "LYCRA" fabric comprises tiny loops, which are generally compatible with releasably engageable hook-like tabs such as those commonly available under the trademark "VELCRO." As will be better understood further herein, these features combine to make this type of fabric ideal for use in this application. Of course, those of ordinary skill in the art will recognize the possible substitutions, such as the less costly nylon based fabrics, as may be made with corresponding sacrifices in the various aspects of the invention. Finally, each laminate may comprise an additional layer 15 of foam material in order to provide increased padding for the patient's foot. The preferred embodiment of the present invention comprises such a layer 15, interposed between the polyurethane and trademark "LYCRA" layers, comprising a 90 mil ester foam. As will be apparent to those of ordinary skill in the art, these laminates also meet the foregoing requirements for water vapor permeability.

As has been noted herein and shown in FIG. 1, the first, or exterior, sheet 11 and the second, or interior, sheet 12 are cut to substantially similar shapes. In particular, the second sheet 12 is cut to form a mirror image of the first sheet 11 and, to simplify manufacture, is preferably cut from the same die in a single cutting stroke. Although not necessary to the manufacturing process, a plurality of apertures 16 may be punched at this time in strategic locations to facilitate RF or heat welding of the sheets one to the other, better understood further herein. The cut sheets 11, 12 are then oriented together, polyurethane side to polyurethane side, and bonded along lines 17 shown in FIG. 1 with RF or heat welding, a process well-known to those of ordinary skill in the art. This bonding process not only results in a unitary construction for the foot wrap, but also allows the formation of a precisely-shaped bladder between the sheets. As shown in FIG. 1, the borders 19 of the bladder of the preferred embodiment of the present invention are shaped through this process to circumscribe the area of the patient's plantar arch from just forward the heel to beneath the phalanges of the toes. Although those of ordinary skill in the art will recognize that infinitely many particular shapes may be produced in this manner, the utility of the preferred shape will be apparent further herein.

As has been noted above, a plurality of tiny apertures 16 are preferably punched to facilitate RF or heat welding. As is known to those of ordinary skill in the art, RF or heat welding is generally accomplished by localizing RF energy or heat in the area 17 of the sheets to be joined. As this bonding process is typically performed by an automated system, the apertures 16 serve to promote alignment of the sheets' edges 18 and provide positional references for the system. In the simplest form, the automated system is provided with posts that extend through the apertures. Although Applicant has found that this two-step process of first cutting the sheets 11, 12 and then bonding them increases the overall success rate for producing high quality wraps 10, those of ordinary skill in the art will recognize many substantially equivalent manufacturing techniques. As examples of these techniques, the first and second sheets 11, 12 may be welded together while simultaneously heat-cutting the border 18 or the sheets 11, 12 may be first RF or heat welded and then cut to shape. Further details of this type of construction may be gleaned from Applicant's U.S. patent application Ser. No. 08/039,574 filed Mar. 25, 1993, which by this reference is incorporated herein.

Figure 2B:
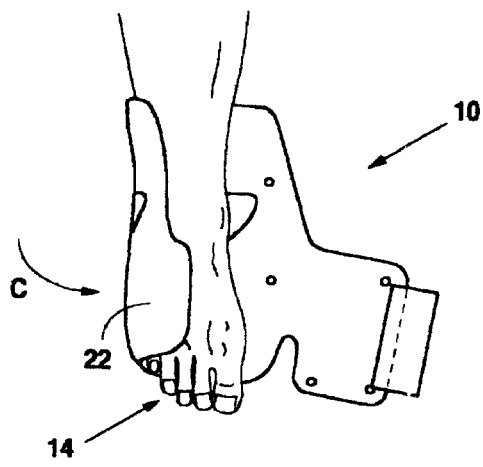
Figure 2C:
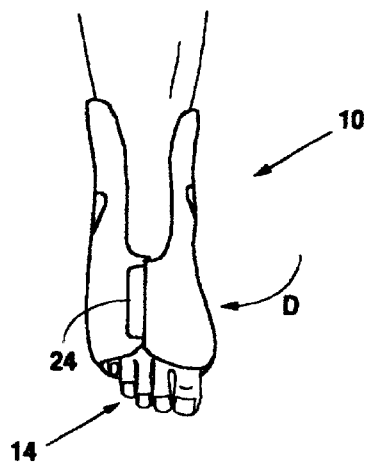

Referring now to FIGS. 2A through 2C, the application of the wrap 10 to a patient's foot 14 is shown. As detailed in FIG. 2A, the wrap 10 is first placed beneath the patient's foot 14. The back flaps 20, 21 are then wrapped about the patient's heel and secured. Preferably a releasably enageageable hook and loop type fastening system, such as that commercially available under the well-known trademark "VELCRO," is employed for this purpose. As shown in FIG. 2B, one front flap 22 of the wrap is then folded over the patient's foot and then, as shown in FIG. 2C, the remaining flap 23 is folded over the first front flap 24 and secured with hook-type tab 24. The wrap 10 is then placed in fluid communication with a medical pumping device such as that previously described—preferably through a provided fitting 25.

In operation, the bladder 13 of the wrap 10 is intermittently inflated in order to produce localized pressure in the area of the patient's wounds. This pressure promotes localized blood flow through the reduction of edema and production of EDRF and local hyperemia. As a result, the healing rate for the wound is dramatically improved.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. In any case, because the scope of the present invention is much broader than any particular embodiment, the foregoing detailed description should not be construed as a limitation of the scope of the present invention, which is limited only by the claims appended hereto.

What is claimed is:

1. A medical wrap for the promotion of diabetic and like wound healing, said medical wrap comprising:
    a multi-layered sheet structure for removable application to a patient's foot, said sheet structure having interposed therein an integral bladder;
    an inlet for fluid inflation of said bladder; and
    said sheet structure being adapted and said bladder being shaped to produce a non-shearing compressive force directly at the patient's first and fifth metatarsal heads upon fluid inflation of said bladder.

2. The medical wrap as recited in claim 1, wherein said multi-layered sheet structure comprises a first sheet and a second sheet, said first sheet forming the exterior of said structure and said second sheet forming the interior of said structure, said second sheet being more extensible than said first sheet.

3. The medical wrap as recited in claim 2, wherein said first and said second sheets each comprise a multi-layered laminate.

4. The medical wrap as recited in claim 3, wherein each said multi-layered laminate comprises an internal padding layer.

5. The medical wrap as recited in claim 4, wherein said padding layer comprises an ester foam.

\* \* \* \* \*